(12) United States Patent
Jean et al.

(10) Patent No.: US 11,614,436 B2
(45) Date of Patent: Mar. 28, 2023

(54) SYSTEM AND METHOD FOR DIAGNOSING A CONDITION OF AN ENGINE

(71) Applicant: PRATT & WHITNEY CANADA CORP., Longueuil (CA)

(72) Inventors: Maurice Jean, Morin-Heights (CA); Nathalie Savard, St-Jean-sur-Richelieu (CA); Sonia Sevigny, Brossard (CA); Stephanie Pronovost, Chambly (CA)

(73) Assignee: PRATT & WHITNEY CANADA CORP., Longueuil (CA)

(*) Notice: Subject to any disclaimer, the term of this patent is extended or adjusted under 35 U.S.C. 154(b) by 861 days.

(21) Appl. No.: 16/439,045

(22) Filed: Jun. 12, 2019

(65) Prior Publication Data

US 2020/0393436 A1 Dec. 17, 2020

(51) Int. Cl.
*G01N 33/28* (2006.01)
*G16C 20/20* (2019.01)
*F01D 25/18* (2006.01)
*G01M 15/14* (2006.01)
*G01N 23/20091* (2018.01)
(Continued)

(52) U.S. Cl.
CPC ......... *G01N 33/2888* (2013.01); *F01D 25/18* (2013.01); *G01M 15/14* (2013.01); *G01N 23/20091* (2013.01); *G01N 23/2252* (2013.01); *G01N 33/2858* (2013.01); *G16C 20/20* (2019.02); *F02K 3/06* (2013.01); *F05D 2220/32* (2013.01); *F05D 2260/80* (2013.01); *F05D 2260/98* (2013.01); *G01N 2223/637* (2013.01); *G01N 2223/652* (2013.01)

(58) Field of Classification Search
CPC ......... G01N 23/20091; G01N 23/2252; G01N 2223/637; G01N 2223/652; G01N 33/28; G01N 33/2835; G01N 33/2858; G01N 33/2888; G16C 20/20; F02K 3/06; F01D 25/18; F01D 21/003; G01M 15/14; F05D 2220/32; F05D 2260/80; F05D 2260/98
See application file for complete search history.

(56) References Cited

U.S. PATENT DOCUMENTS 5,889,200 A 3/1999 Centers et al.
9,897,582 B2 2/2018 Jean et al.
(Continued)

FOREIGN PATENT DOCUMENTS

WO 9414049 6/1994

OTHER PUBLICATIONS

Extended European Search Report dated Nov. 11, 2020 in counterpart EP application.

*Primary Examiner* — Loren C Edwards
(74) *Attorney, Agent, or Firm* — Norton Rose Fulbright Canada LLP (57) ABSTRACT

A method and system for diagnosing a condition of an engine is described herein. The method comprises obtaining a sample of lubricating fluid from the engine, filtering the sample to obtain a plurality of particles from the lubricating fluid, determining surface chemical compositions for the plurality of particles, comparing the surface chemical compositions to at least one reference chemical composition associated with corrosion of the engine, determining a level of corrosion of the engine based on the comparing, and diagnosing a condition of the engine based on the level of corrosion.

20 Claims, 4 Drawing Sheets

(51) Int. Cl.
*G01N 23/2252* (2018.01)
*F02K 3/06* (2006.01)

(56) References Cited

U.S. PATENT DOCUMENTS

2003/0196632 A1 10/2003 Reischman et al.
2017/0159485 A1* 6/2017 Jean ..................... G01M 15/14

* cited by examiner

SYSTEM AND METHOD FOR DIAGNOSING A CONDITION OF AN ENGINE

TECHNICAL FIELD

The present disclosure relates generally to methods and systems for diagnosing a condition of an engine, for example based on a level of corrosion of engine components.

BACKGROUND OF THE ART

The analysis of engine oil or other lubricant for the purpose of identifying premature component wearing has been performed for several decades using optical atomic spectroscopy (e.g., atomic emission spectroscopy (AES), as well as atomic absorption spectroscopy (AAS)). This technology was the basis for the military aviation's Spectroscopic Oil Analysis Program (SOAP). However, it has certain disadvantages, such as a lack of repeatability among different equipment and an inability to analyze particles greater than 5 μm in diameter. Furthermore, optical atomic spectroscopy is an elemental analysis of the total oil sample and typically does not characterize individual particles in the sample.

Other approaches have since been proposed, whereby individual particles may be characterized and classified based on their chemical composition. However, improvements are needed.

SUMMARY

In accordance with a first broad aspect, there is provided a method for diagnosing a condition of an engine. The method comprises obtaining a sample of lubricating fluid from the engine, filtering the sample to obtain a plurality of particles from the lubricating fluid, determining surface chemical compositions for the plurality of particles, comparing the surface chemical compositions to at least one reference chemical composition associated with corrosion of the engine, determining a level of corrosion of the engine based on the comparing, and diagnosing a condition of the engine based on the level of corrosion.

In accordance with another broad aspect, there is provided a system for diagnosing a condition of an engine. The system comprises at least one processor and a memory having stored thereon program code executable by the at least one processor for obtaining input data generated from imaging a plurality of particles filtered from a sample of lubricating fluid from the engine, determining surface chemical compositions for the plurality of particles based on the input data, comparing the surface chemical compositions to at least one reference chemical composition associated with corrosion of the engine, determining a level of corrosion of the engine based on the comparing, and diagnosing a condition of the engine based on the level of corrosion.

In accordance with yet another broad aspect, there is provided a non-transitory computer readable medium having stored thereon program code executable by a processor for carrying out the methods described herein.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Aircraft engines and/or engine components are sometimes affected by corrosion, such as those caused by oxidation as well as other corrosion mechanisms. The causes of the corrosion are varied, including poorly preserved alloys or aggressive environments. The analysis of particles in oil is typically used for debris, and is based on chemical composition and/or geometric parameters. However, the presence of corrosion is not directly measureable via these techniques.

Some techniques for determining the presence of corrosion include a visual inspection of the engine components, for example using a borescope or by disassembling the engine. These techniques may be used only when the corrosion process is at a fairly advanced stage.

There are described herein methods and systems for determining a level of corrosion of engine components through the analysis of lubricating fluid. The level of corrosion of engine components may be determined by looking for signatures or patterns in surface chemical composition of particles in engine oil, the signatures or patterns determined using a combination of visual inspection and particle analysis. These methods and systems for determining a level of corrosion of engine components using fluid analysis techniques may be used for engine diagnostics, in particular for gas turbine engines.

Figure 1:
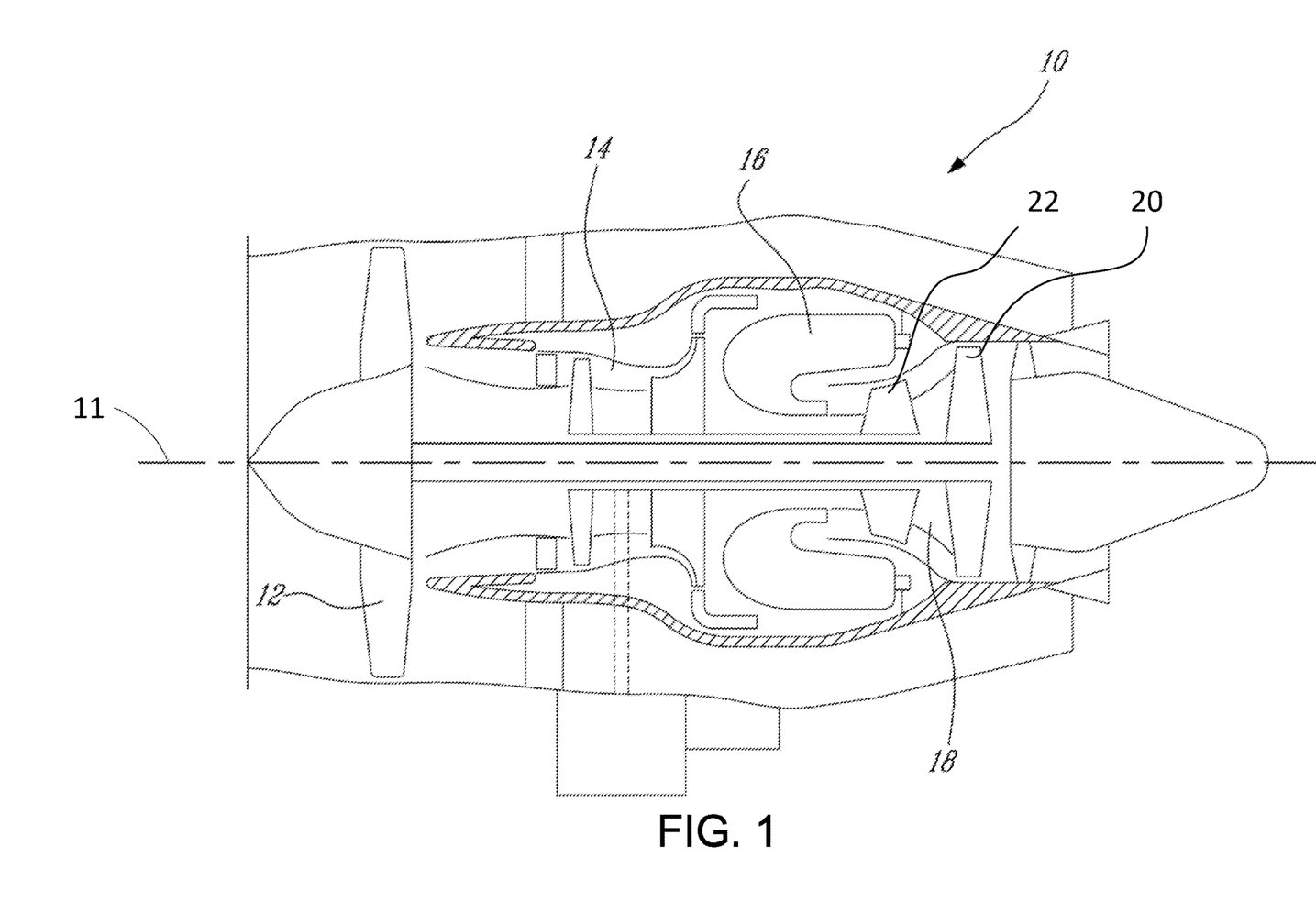
FIG. 1 illustrates an example of a gas turbine engine, in accordance with some embodiments.

FIG. 1 illustrates an example of a gas turbine engine 10 to which the methods and systems described herein may be applied. Note that while engine 10 is a turbofan engine, the methods and systems described herein may be applicable to turboprop, turboshaft, and other types of gas turbine engines. Engine 10 generally comprises in serial flow communication: a fan 12 through which ambient air is propelled, a compressor section 14 for pressurizing the air, a combustor 16 in which the compressed air is mixed with fuel and ignited for generating an annular stream of hot combustion gases, and a turbine section 18 for extracting energy from the combustion gases. Axis 11 defines an axial direction of the engine 10. In some embodiments, a low pressure spool is composed of a low pressure shaft and a low pressure turbine 20. The low pressure shaft drives the fan 12. A high pressure spool is composed of a high pressure turbine 22 attached to a high pressure shaft, which is connected to the compressor section 14.

In some embodiments, the disclosed methods and systems may provide diagnostic and analytical tools based on analysis of particles in fluids, such as engine oil or other lubricants and may provide advance detection of premature wear on specific engine parts and/or detection of failure mechanisms. In some embodiments, the disclosed methods and systems may be suitable for failure prediction for gas turbine engines operating in the field. The disclosed methods and systems may be used for prediction of other wear events including prediction of events other than failure using analysis of any suitable lubricating fluid of the engine. The disclosed methods and systems may also be used to detect any abnormal behavior of an engine component in contact with a lubrication fluid system, for example.

Figure 2:
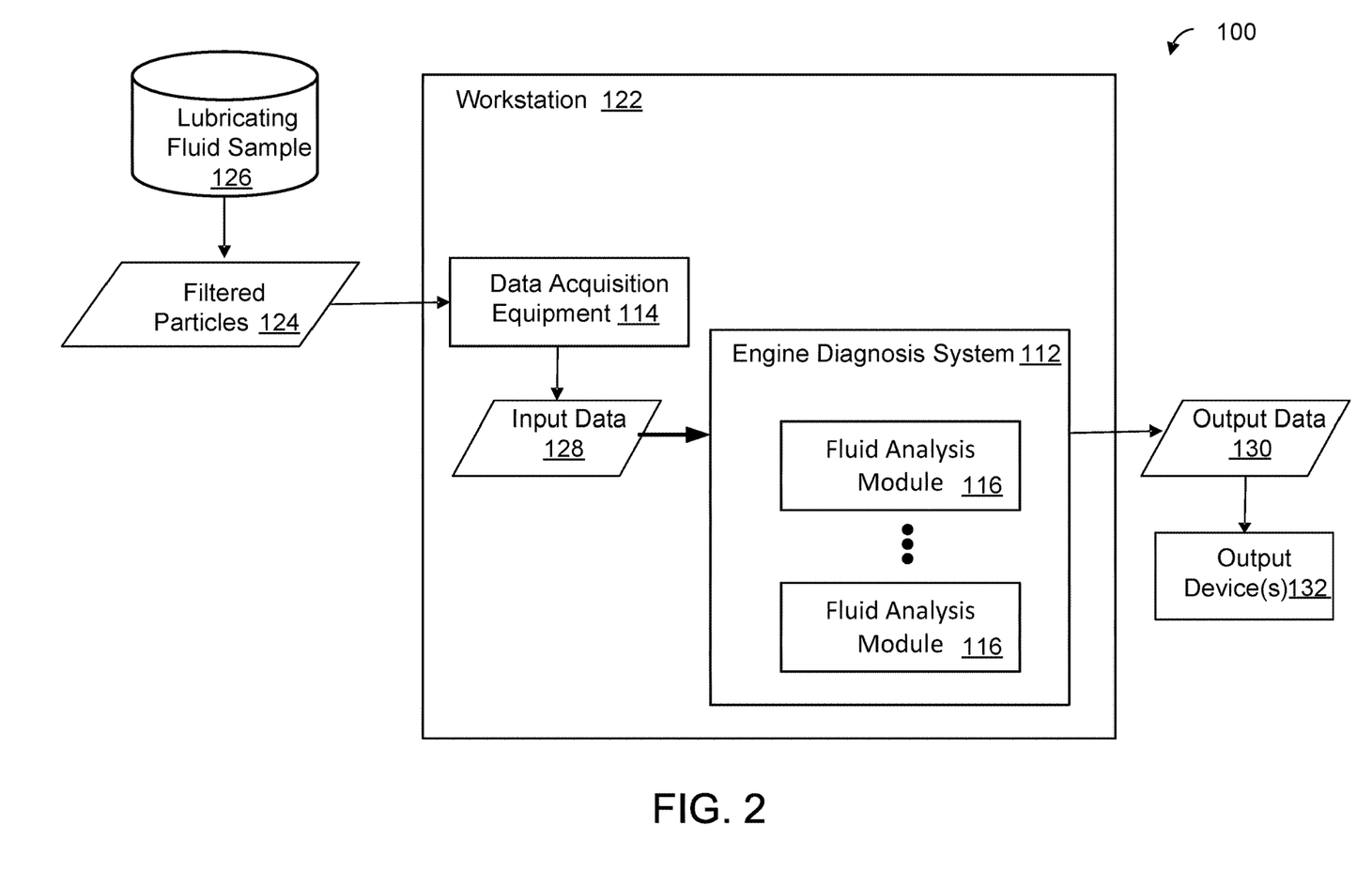
FIG. 2 is a block diagram of an example system for diagnosing a condition of an engine, in accordance with some embodiments.

FIG. 2 is a schematic diagram of an exemplary system 100 for diagnosing a condition of an engine such as the engine 10 and which uses a fluid for lubricating some of its components, such as bearings. System 100 comprises an engine diagnostic system 112 and suitable data acquisition equipment 114 of known or other type. The engine diagnosis system 112 may comprise one or more fluid analysis modules 116 configured to determine a level of corrosion of the engine. In some embodiments, the fluid analysis module 116 is configured for determining a level of corrosion of a given component made of a given material, for example M50 (i.e. steel). In some embodiments, a separate fluid analysis module 116 is provided to determine the level of corrosion of each one of a plurality of components, each made of a given material. For example, a first fluid analysis module 116 is configured to determine the level of corrosion of a gear made of low alloy steel, and a second fluid analysis module 116 is configured to determine the level of a gear box made of a magnesium-based material. Other implementations are also considered.

The engine diagnosis system 112 and data acquisition equipment 114 may be considered part of a workstation 122, such as for example a Scanning Electron Microscope (SEM). Accordingly, data acquisition equipment 114 may comprise an SEM and other related devices, although any other suitable devices/methods for extracting the relevant information from particles 124 filtered from lubricating fluid sample 126 may be used. In some embodiments, data acquisition equipment 114 may comprise an SEM and an X-Ray Fluorescence (XRF) detector for carrying out particle analysis. In some embodiments, the data acquisition equipment 114 may comprise an SEM and an energy dispersive x-ray detector for carrying out particle analysis. In some embodiments, an automated SEM is used and may not require the presence of a human to select the particle(s) 124 that will be analyzed. In some embodiments, software and/or hardware included in workstation 122 may automatically recognize the presence of a particle 124 and may then automatically move a stage and/or an electron beam to the particle(s) 124 on which to perform the analysis.

System 100 may be used to conduct analysis of particles 124 filtered from lubricating fluid sample 126. Data acquisition equipment 114 may be used to analyze filtered particles 124 and generate input data 128. Input data 128 may be processed using engine diagnosis system 112 in order to generate output data 130. In some embodiments, output data 130 may be representative of a diagnosis of the condition of the engine and may be delivered to a user of system 100 or other authorized party via output device(s) 132 (e.g., one or more screens and/or printers) for displaying and/or otherwise providing a report of the result(s) of the diagnosis. In some embodiments, output data 130 may be representative of a level of corrosion of the engine based on an analysis of the fluid. The output data 130 may be used by one or more other systems to diagnose a condition of an engine based on the level of corrosion.

System 100 may include one or more input devices (e.g., keyboard and mouse) for receiving user input, as well as one or more data ports and/or communication ports for receiving and/or transmitting data (e.g., wirelessly or through wired connections) from/to other processors, systems and/or devices. Processing of input data 128 by engine diagnosis system 112 may make use of reference data for comparison purpose. It is understood that processing of input data 128 may be performed using one or more processors external to workstation 122.

Figure 3:
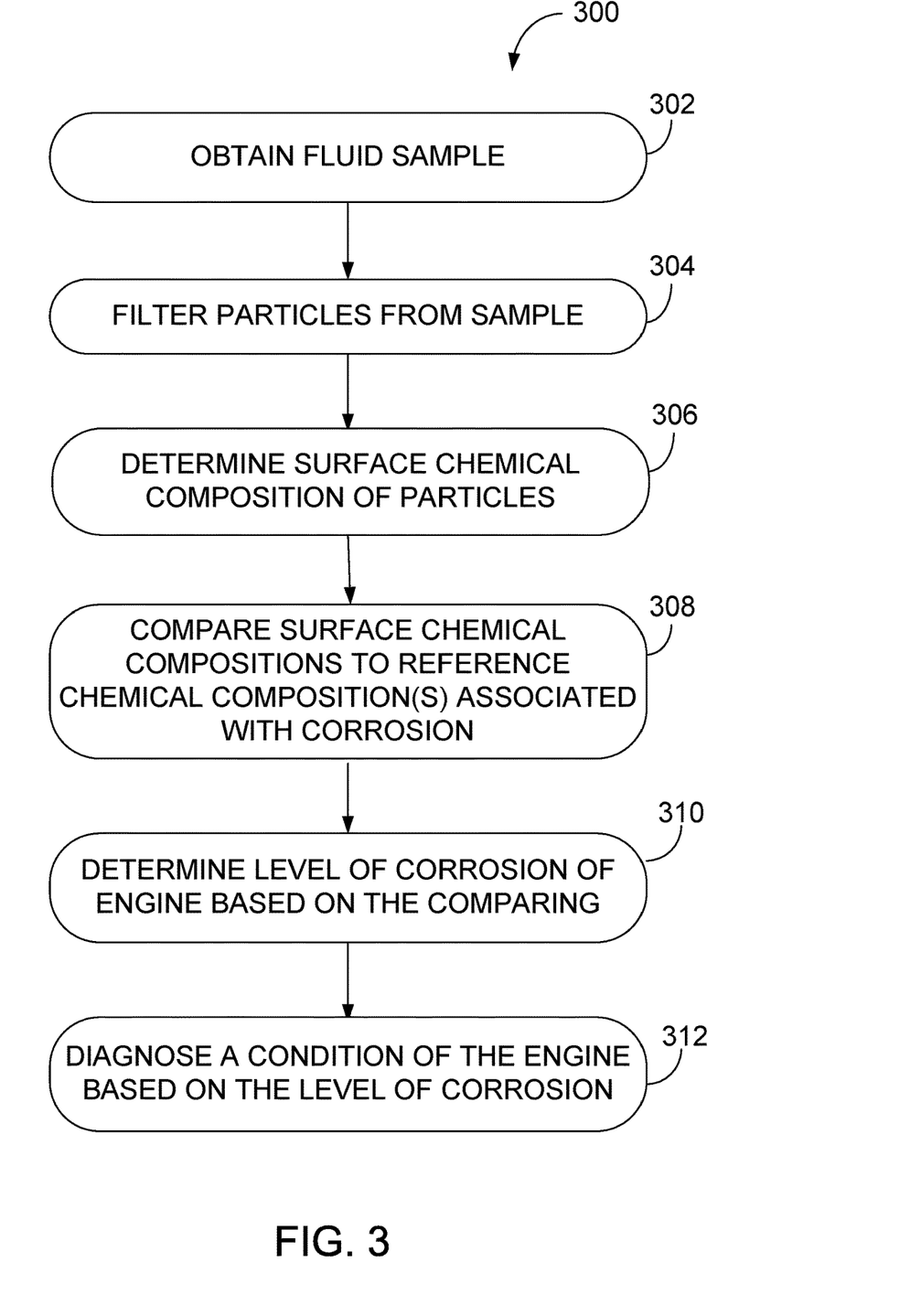
FIG. 3 is a flowchart of an example method for diagnosing a condition of an engine, in accordance with some embodiments.

Referring to FIG. 3, there is illustrated a flowchart of an example method 300 for diagnosing a condition of an engine, such as engine 10. At step 302, a sample of lubricating fluid is obtained. For example, a sample of oil is obtained from the engine under diagnosis. In the case of a fluid sample from an aircraft engine, the fluid sample may be collected by an aircraft operator. More than one sample may be obtained. The amount of fluid sample obtained (e.g., 25 mL or less) may be selected in order to obtain a certain number of particles. For example, it may be known or expected that a given engine should have a certain density of particles in the fluid after a certain number of operating hours. The volume of fluid sample obtained may thus be determined in order to obtain an optimal quantity of particles. The frequency of sampling may be determined based on the operating hours per year, the maturity of the engine, the typical behavior of the engine type and/or the history of unscheduled engine removal for that engine type, for example. Any known or other engine fluid sampling method may be used, such as but not limited to pressurized line sampling, drop tube sampling, and drain port sampling.

At step 304, the sample of fluid is filtered to obtain a plurality of particles from the sample. Filtering may be performed using various techniques. For example, a collected fluid sample may be filtered using a very fine filter, such as a 0.22 μm filter, in order to filter out even very small particles (e.g., particles sized as small as 0.5 μm in diameter or smaller). Using such a filter, a sample of about 25 mL may produce a surface sample of about 16 mm in diameter. The particles obtained may range in size from about 0.5 μm to about 1600 μm, for example, although smaller or larger particles may also be obtained. The volume of fluid sample filtered and the size of the sample prepared may vary, such as according to the number of particles in the fluid. The volume of fluid sample that is filtered may be determined based on the type of engine and/or the expected normal levels of particles in the fluid. In some examples, the obtained density of particles may be 500 particles per $mm^2$. Other densities may also be used.

At step 306, the particles obtained from the sampling of step 304 are analyzed to determine surface chemical compositions. The analysis is based on input data generated from one or more imaging procedure performed on the filtered particles. The imaging procedure may be any technology capable of providing a spectral signature, such as an emission spectrum plotted as a function of wavelength or frequency. For example, the input data may comprise a set of peaks along an electromagnetic emission spectrum obtained using energy-dispersive x-ray (EDX) or fluorescence imaging. Any other suitable imaging technique for determining surface chemical composition of particles may also be used. In some embodiments, the input data also includes respective geometric parameters for the particles, which may be used to further categorize the particles under analysis.

In some embodiments, more than one imaging technique is used to generate the input data. For example, optical imaging may be used to determine geometric parameters of the particles and EDX spectroscopy may be used to obtain the surface chemical composition. The two or more imaging procedures may be performed at the workstation 122 using the data acquisition equipment 114. Alternatively, one imaging procedure is performed at a first workstation 122 using first data acquisition equipment 114 and another imaging procedure is performed at a second workstation using second data acquisition equipment.

A subset of the particles (e.g., 10% or less) may be analyzed to determine the features (such as surface chemical composition) while ensuring a good representation of the whole sample is captured. The analysis of the subset may be normalized to reflect the result for the full sample. For an average fluid sample, about 1500 to 2000 particles may be analyzed. Suitable image analyzer software, such as those conventionally used with SEM, may be used to collect data about particle composition. Analysis of each particle may produce a respective set of data for that particle, for example there may be up to 70 data points for each particle, the data describing various features of the particle (e.g., size, shape and composition, among others).

At step 308, the surface chemical compositions as determined at step 306 are compared to one or more reference chemical compositions. The reference chemical compositions are associated with corrosion/oxidation of certain components in an engine. The comparison serves to detect a variation in surface composition of certain alloys when they undergo corrosion. For example, particles from aluminum-based components may initially have a surface composition of 95% aluminum and 5% copper. Once the component (or engine) undergoes corrosion, the surface composition of the particle changes such that the proportion of copper increases, for example to 8%, 9%, or 10%, and the proportion of aluminum decreases, for example to 92%, 91%, or 90%, respectively. Note that despite the variations in surface composition, there may be very little variation to the particle's inner matrix. The same pattern can be observed for particles that are initially composed of magnesium and zinc, where magnesium forms a majority of the surface composition and zinc forms a minority of the surface composition. Corrosion may cause an increase in zinc and a decrease in magnesium. In another example, particles initially having a surface composition of cast iron and chrome will tend to form chromium oxide on its surface due to oxidation, with a reduction in the iron on the surface of the particle. For each of these examples, the reference chemical composition corresponds to the surface chemical composition of particles having undergone changes due to corrosion.

In some embodiments, one or more of the reference chemical compositions comprise an alloy composed of two or more elements. For example, one of the elements may be a first metal that decreases in concentration due to corrosion and that forms more than 50% of the alloy. Examples are aluminum, iron, magnesium, nickel, and cobalt. In some embodiments, one of the elements may be a second metal that increases in concentration due to corrosion and forms less than 50% of the alloy. Examples are copper, chromium, and zinc.

The reference chemical compositions may be determined using a combination of fluid analysis and visual inspection of engines and/or engine components. For example, fluid analysis may be performed when various levels of corrosion are observed on the engine and/or engine components. Similarly, visual inspection may be performed when certain surface chemical compositions are detected via fluid analysis. The surface chemical compositions of particles in the lubricating fluid of known corroded engines may be compared with the surface chemical compositions of particles in the lubricating fluid of known uncorroded engines to identify differences in surface chemical compositions of the particles that can be directly associated with corrosion.

In some embodiments, visual inspection and fluid analysis are performed several times over the operating life of a plurality of engines, in order to identify trends and/or patterns in the variation of surface chemical composition of particles in the fluid as they correlate to different stages of corrosion of the engine and/or engine components. In some embodiments, the reference chemical compositions represent an average or mean of the results of the visual inspection and fluid analysis, as observed for the plurality of engines. In some embodiments, different reference chemical compositions are associated with different levels of corrosion.

At step 310, a level of corrosion of the engine and/or engine component is determined based on the comparison between the surface chemical compositions of the filtered particles and the reference chemical composition(s).

In some embodiments, determining a level of corrosion comprises determining whether or not there is corrosion. In other words, the determination is a binary evaluation with the outcome corresponding to a positive or a negative result. For example, corrosion may be detected when a certain number of particles from the fluid sample analyzed match one of the reference chemical compositions. An example is shown in Table 1 below.

TABLE 1

| # of particles with a match | Result |
|---|---|
| <50 | No corrosion |
| >51 | Corrosion |

The number of particles used as the threshold for corrosion in Table 1 (as well as any other values provided herein) is for illustrative purposes only and should not be construed as limiting. In some embodiments, the number of particles that match will be associated with various levels of corrosion. An example is shown in Table 2 below.

TABLE 2

| # of particles with a match | Result |
|---|---|
| 0-25 | No Corrosion |
| 26-50 | Low Corrosion |
| 51-75 | Medium Corrosion |
| >76 | High Corrosion |

In some embodiments, different reference chemical compositions are associated with different levels of corrosion. An example is illustrated in Table 3 below.

TABLE 3

| Reference Chemical Composition | Level of Corrosion |
|---|---|
| 93% Al; 5% Cu | Level 1 |
| 92% Al; 7% Cu | Level 2 |
| 91% Al; 9% Cu | Level 3 |

In some embodiments, the level of corrosion is determined using a combination of the number of particles and the reference chemical composition. An example is shown in Table 4 below.

TABLE 4

| # of particles with a match | Reference Chemical Composition | Level of Corrosion |
| --- | --- | --- |
| >50 particles | 93% Al; 5% Cu | Level 1 |
| >40 particles | 92% Al; 7% Cu | Level 2 |
| >30 particles | 91% Al; 9% Cu | Level 3 |

In the example of Table 4, a threshold for number of particles is associated with a given reference chemical composition in order to result in a given level of corrosion. The threshold is shown to decrease as the proportion of aluminum decreases and the proportion of copper increases, as this trend in variation is indicative of increased corrosion. Therefore, less particles are needed to confirm corrosion. Other implementations are also considered.

In some embodiments, a match corresponds to an exact match of a surface chemical composition to a reference chemical composition. In other words, a surface chemical composition of 90% Al; 10% Cu will constitute a match with a reference chemical composition of 90% Al; 10% Cu but not with a reference chemical composition of 92% Al; 8% Cu or 94% Al; 6% Cu.

In some embodiments, a match corresponds to a difference between the surface chemical composition and the reference chemical composition that is less than a given threshold, such as 0.9% (e.g. 93.1%-93.9% Al will match with 93% Al), 1.0%, 1.5%, or another value for a given element in the surface chemical composition.

Referring back to FIG. 3, at step 312, a condition of the engine may be diagnosed based on the level of corrosion. The condition may comprise a number of remaining flight hours for the engine, an expected need for engine maintenance, a level of impact of the corrosion on the engine, a reduction in efficiency of the engine (i.e. 10%, 25%, 50%, etc), and the like. In some embodiments, diagnosing a condition of the engine may comprise determining an action to be taken, such as performing a maintenance, performing a visual inspection, changing the lubricating fluid, monitoring the engine, and the like.

Table 5 below is an example lookup table that may be used for engine diagnosis, for example by the engine diagnosis system 112.

TABLE 5

| Corrosion Level | Remaining Flight Hours before next maintenance |
| --- | --- |
| Level 1 | >500 hrs |
| Level 2 | 250-500 hrs |
| Level 3 | <250 hrs |

Table 6 below is another example lookup table that may be used for engine diagnosis.

TABLE 6

| Corrosion Level | Level of impact of Corrosion on the engine |
| --- | --- |
| Level 1 | Low |
| Level 2 | Medium |
| Level 3 | High |

More or less than three levels, as shown in Table 6, may be used to diagnose the condition of the engine. The number of levels for diagnosing the condition of the engine will generally correspond to the number of levels of corrosion, although more or less granularity may be provided for either one of the corrosion levels and the engine conditions without requiring a same level of granularity for the other one of the corrosion levels and the engine conditions.

In some embodiments, the level of corrosion is associated with two or more specific conditions of the engine, such as a general level of impact, an estimated number of flight hours before a next maintenance, an estimated efficiency of the engine, and the like.

Reference data may be used to establish the condition of the engine as a function of the corrosion. For example, reference engines from a common engine family having run a certain number of hours using a given lubricating fluid may be analyzed to obtain the reference data. In some embodiments, the reference data is presented as one or more averages for a plurality of reference engines. The reference engines used for the reference data may form part of a common family with the engine under analysis. An engine family may be defined by any engine characteristic, such as type, model, operating principle, configuration, use, performance, thrust, torque, speed, power, etc. An engine family may also be defined by two or more engine features. For example, a family may correspond to turboprop engines, or turboprop engines in use in aircraft, or turboprop engines in use in aircraft and weighing between 150 and 450 kg. In another example, a family may correspond to a specific model or series, such as the PT-6 Series from Pratt & Whitney Canada. In some embodiments, a family may comprise sub-families, i.e. the family has at least one common engine characteristic and each sub-family has at least one additional common engine characteristic. Various combinations may be used.

In some embodiments, the reference data is presented as a percentage of selected engines matching one or more events. For example, out of 50 reference engines selected, i.e. comprising a similar level of corrosion per sample of lubricating fluid, the reference data may be presented as: 100% operated 200 hours without any problems, 91% operated 500 hours without any problems, 73% operated 600 hours without any problems, 10% operated 750 hours without any problems. Other events may also be used in this format.

In some embodiments, diagnosing a condition of the engine, as per step 312, comprises assigning a rating to the engine. Various types of engine rating systems may be used, and comprise any number of rating levels, such as two, three, four, and more. The ratings may be associated with an expected time until maintenance, or an expected time until breakdown. The rating may be determined using only the reference data of the reference engines, or a combination of reference data of the reference engines and historical/current data of the engine under analysis. For example, if the expected time until maintenance is 600 hours, the probability of achievement will be 73% based on the reference engines. Other rating systems may readily apply.

In some embodiments, diagnosing a condition of the engine comprises determining a source of the corrosion in the engine. For example, the nature of the dominant metal covering the surface of the particle that matches with the reference chemical composition is indicative of the source of the particle. A particle covered mainly in aluminum will likely originate from a component made from aluminum, such as a bearing. The source of corrosion may be used to recommend a course of action, as a function of the source of corrosion and its potential impact on the engine. Components that are more critical may lead to an earlier maintenance while components that are less critical may lead to a later maintenance. Other implementations are also considered.

In some embodiments, the condition of the engine is used to determine whether an aircraft having an engine with a given level of corrosion should be deployed or not for a mission. In some embodiments, the method 300 further comprises a step of taking a maintenance action based on the diagnosing, such as but not limited to issuing a report on the level of corrosion of the engine, setting a flag indicating a need for inspection, performing further inspection of the engine, and the like.

Figure 4:
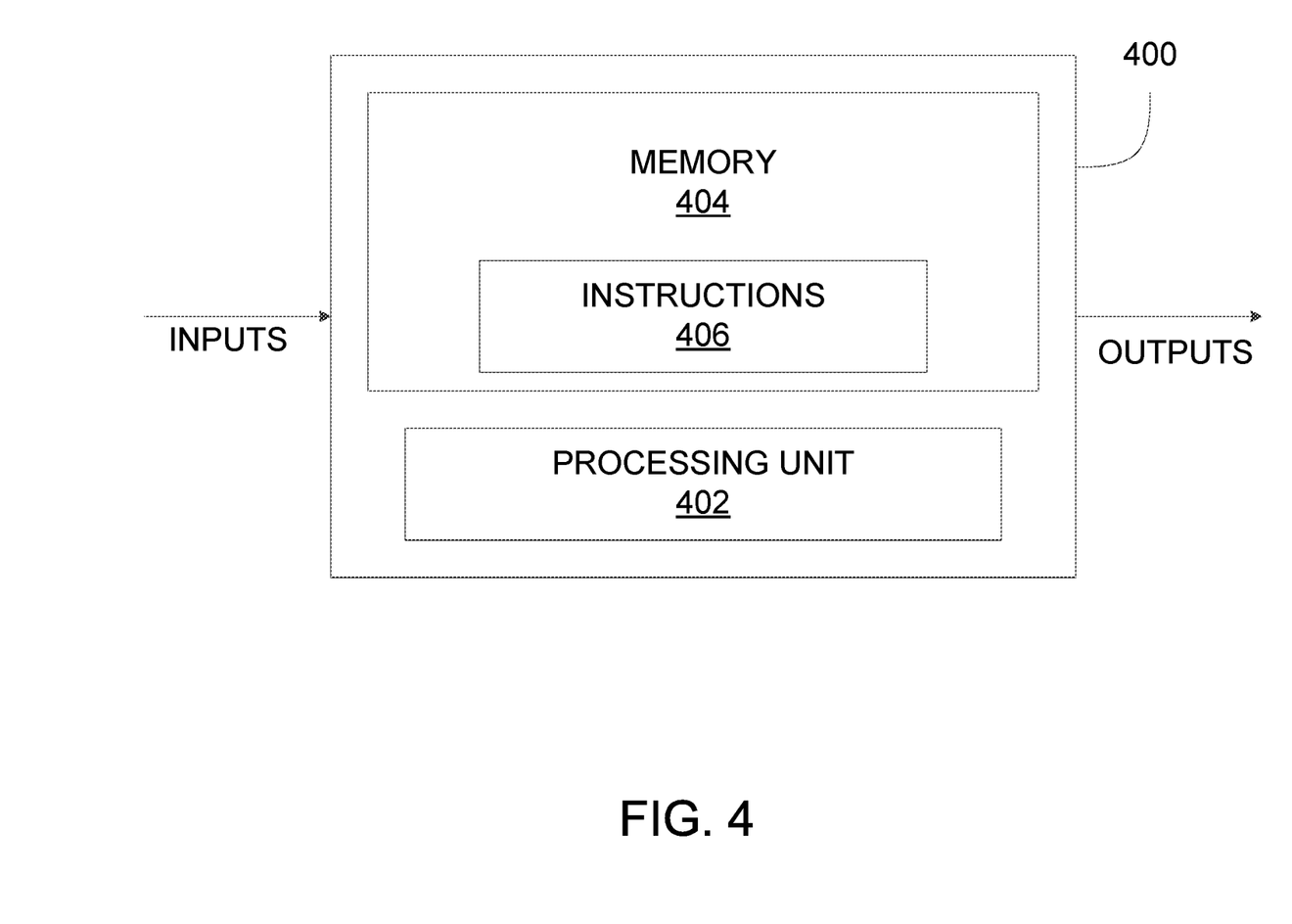
FIG. 4 is a block diagram of an example computing device for implementing a method for determining a level of corrosion of an engine and/or engine component, in accordance with some embodiments.

FIG. 4 is an example embodiment of a computing device 400 for implementing the engine diagnosis system 112 and/or the fluid analysis module 116 described above. The computing device 400 comprises a processing unit 402 and a memory 404 which has stored therein computer-executable instructions 406. The processing unit 402 may comprise any suitable devices configured to cause a series of steps to be performed such that instructions 406, when executed by the computing device 400 or other programmable apparatus, may cause the functions/acts/steps specified in the methods described herein to be executed. The processing unit 402 may comprise, for example, any type of general-purpose microprocessor or microcontroller, a digital signal processing (DSP) processor, a CPU, an integrated circuit, a field programmable gate array (FPGA), a reconfigurable processor, other suitably programmed or programmable logic circuits, or any combination thereof.

The memory 404 may comprise any suitable known or other machine-readable storage medium. The memory 404 may comprise non-transitory computer readable storage medium, for example, but not limited to, an electronic, magnetic, optical, electromagnetic, infrared, or semiconductor system, apparatus, or device, or any suitable combination of the foregoing. The memory 404 may include a suitable combination of any type of computer memory that is located either internally or externally to device, for example random-access memory (RAM), read-only memory (ROM), electro-optical memory, magneto-optical memory, erasable programmable read-only memory (EPROM), and electrically-erasable programmable read-only memory (EEPROM), Ferroelectric RAM (FRAM) or the like. Memory 404 may comprise any storage means (e.g., devices) suitable for retrievably storing machine-readable instructions 406 executable by processing unit 402. In some embodiments, the memory 404 stores one or more reference chemical composition associated with corrosion. In some embodiments, the memory 404 stores one or more corrosion level associated with the reference chemical compositions. In some embodiments, the memory 404 stores reference data from reference engines, and/or one or more lookup tables associating various levels of corrosion with corresponding engine conditions.

The methods and systems for diagnosing a condition of an engine and/or for determining a level of corrosion as described herein may be implemented in a high level procedural or object oriented programming or scripting language, or a combination thereof, to communicate with or assist in the operation of a computer system, for example the computing device 400. Alternatively, the methods and systems for diagnosing a condition of an engine and/or for determining a level of corrosion may be implemented in assembly or machine language. The language may be a compiled or interpreted language. Program code for implementing the methods and systems for diagnosing a condition of an engine and/or for determining a level of corrosion may be stored on a storage media or a device, for example a ROM, a magnetic disk, an optical disc, a flash drive, or any other suitable storage media or device. The program code may be readable by a general or special-purpose programmable computer for configuring and operating the computer when the storage media or device is read by the computer to perform the procedures described herein. Embodiments of the methods and systems for diagnosing a condition of an engine and/or for determining a level of corrosion may also be considered to be implemented by way of a non-transitory computer-readable storage medium having a computer program stored thereon. The computer program may comprise computer-readable instructions which cause a computer, or more specifically the processing unit 402 of the computing device 400, to operate in a specific and predefined manner to perform the functions described herein.

Computer-executable instructions may be in many forms, including program modules, executed by one or more computers or other devices. Generally, program modules include routines, programs, objects, components, data structures, etc., that perform particular tasks or implement particular abstract data types. Typically the functionality of the program modules may be combined or distributed as desired in various embodiments.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure.

Various aspects of the methods and systems for detecting a fault may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments. Although particular embodiments have been shown and described, it will be obvious to those skilled in the art that changes and modifications may be made without departing from this invention in its broader aspects. The scope of the following claims should not be limited by the embodiments set forth in the examples, but should be given the broadest reasonable interpretation consistent with the description as a whole.

The invention claimed is:

1. A method for diagnosing a condition of an engine, the method comprising:
    obtaining a sample of a lubricating fluid from the engine;
    filtering the sample to obtain a plurality of filtered particles from the lubricating fluid;
    determining a plurality of surface chemical compositions for the plurality of filtered particles;
    receiving at least one reference chemical composition of reference particles having undergone changes due to corrosion;
    performing a comparison between the surface chemical compositions and the at least one reference chemical composition;
    determining a level of corrosion of the engine based on the comparison; and
    diagnosing a condition of the engine based on the level of corrosion.

2. The method of claim 1, wherein the at least one reference chemical composition comprises an alloy composed of at least two elements.

3. The method of claim 2, wherein one of the at least two elements is a first metal that decreases in concentration due to corrosion and that forms more than 50% of the alloy.

4. The method of claim 3, wherein the first metal is one of aluminum, iron, and magnesium.

5. The method of claim 2, wherein one of the at least two elements is a second metal that increases in concentration due to corrosion and that forms less than 50% of the alloy.

6. The method of claim 5, wherein the second metal is one of copper, chromium, and zinc.

7. The method of claim 1, wherein determining the level of corrosion of the engine based on the comparison comprises determining the level of corrosion as a function of a number of the plurality of filtered particles that match the at least one reference chemical composition.

8. The method of claim 7, wherein a respective one of the plurality of filtered particles is found to match the at least one reference chemical composition when a respective surface chemical composition differs from the at least one reference chemical composition by a value that is less than a threshold.

9. The method of claim 1, wherein the at least one reference chemical composition comprises a plurality of reference chemical compositions each associated with one of a plurality of corrosion levels, and wherein determining the level of corrosion comprises selecting from the plurality of corrosion levels.

10. A system for diagnosing a condition of an engine, the system comprising:
at least one processor; and
a non-transitory computer readable storage medium having stored thereon program code executable by the at least one processor for:
obtaining input data generated from imaging a plurality of filtered particles filtered from a sample of lubricating fluid from the engine;
determining a plurality of surface chemical compositions for the plurality of filtered particles based on the input data;
receiving at least one reference chemical composition of reference particles that have undergone changes due to corrosion;
performing a comparison between the surface chemical compositions and the at least one reference chemical composition;
determining a level of corrosion of the engine based on the comparison; and
diagnosing a condition of the engine based on the level of corrosion.

11. The system of claim 10, wherein the at least one reference chemical composition comprises an alloy composed of at least two elements.

12. The system of claim 11, wherein one of the at least two elements is a first metal that decreases in concentration due to corrosion and that forms more than 50% of the alloy.

13. The system of claim 12, wherein the first metal is one of aluminum, iron, and magnesium.

14. The system of claim 11, wherein one of the at least two elements is a second metal that increases in concentration due to corrosion and that forms less than 50% of the alloy.

15. The system of claim 14, wherein the second metal is one of copper, chromium, and zinc.

16. The system of claim 10, wherein determining the level of corrosion of the engine based on the comparison comprises determining the level of corrosion as a function of a number of the plurality of filtered particles that match the at least one reference chemical composition.

17. The system of claim 16, wherein a respective one of the plurality of filtered particles is found to match the at least one reference chemical composition when a respective surface chemical composition differs from the at least one reference chemical composition by a value that is less than a threshold.

18. The system of claim 10, wherein the at least one reference chemical composition comprises a plurality of reference chemical compositions each associated with one of a plurality of corrosion levels, and wherein determining the level of corrosion comprises selecting from the plurality of corrosion levels.

19. A method for determining a level of corrosion of an engine, the method comprising:
obtaining input data generated from imaging a plurality of filtered particles filtered from a sample of lubricating fluid from the engine;
determining a plurality of surface chemical compositions for the plurality of filtered particles based on the input data;
receiving at least one reference chemical composition of reference particles that have undergone changes due to corrosion;
performing a comparison between the surface chemical compositions and the at least one reference chemical composition; and
determining a level of corrosion of the engine based on the comparison.

20. The method of claim 19, wherein the at least one reference chemical composition comprises a plurality of reference chemical compositions each associated with one of a plurality of corrosion levels, and wherein determining the level of corrosion comprises selecting from the plurality of corrosion levels.

* * * * *